(12) United States Patent
Weng

(10) Patent No.: US 6,813,794 B2
(45) Date of Patent: Nov. 9, 2004

(54) VIBRATORY ELECTRIC TOOTHBRUSH

(76) Inventor: Shixing Weng, 11 Metzak Dr., Brampton, Ontario (CA), L6Z 4N3

( * ) Notice: Subject to any disclaimer, the term of this patent is extended or adjusted under 35 U.S.C. 154(b) by 234 days.

(21) Appl. No.: 10/270,425

(22) Filed: Oct. 15, 2002

(65) Prior Publication Data

US 2004/0068809 A1 Apr. 15, 2004

(51) Int. Cl.[7] ............................................... A61C 17/22
(52) U.S. Cl. ......................................... 15/22.4; 15/22.1
(58) Field of Search ................................ 15/22.1, 22.4

(56) References Cited

U.S. PATENT DOCUMENTS

| | | | | |
|---|---|---|---|---|
| 1,832,519 A | * | 11/1931 | Wheat et al. ................. 15/22.4 |
| 1,887,913 A | * | 11/1932 | Bell ............................. 403/292 |
| 2,063,801 A | * | 12/1936 | Gano Jr. ....................... 15/22.4 |
| 2,439,262 A | * | 4/1948 | Gresham et al. .............. 62/414 |
| 3,029,651 A | * | 4/1962 | Flatt ............................... 74/48 |
| 3,182,345 A | * | 5/1965 | Smith ........................ 15/176.6 |
| 3,562,566 A | * | 2/1971 | Kircher ......................... 310/80 |
| 3,699,952 A | * | 10/1972 | Waters et al. .................. 601/18 |
| 3,945,076 A | * | 3/1976 | Sung ............................ 15/22.1 |
| 3,978,852 A | * | 9/1976 | Annoni ........................ 601/142 |
| 4,149,291 A | * | 4/1979 | Stoltz .......................... 15/22.1 |
| 4,175,299 A | * | 11/1979 | Teague et al. ................ 15/22.1 |
| D278,481 S | * | 4/1985 | Ditgen ......................... D4/104 |
| D297,784 S | * | 9/1988 | Moret ........................... D4/101 |
| 4,811,445 A | * | 3/1989 | Lagieski et al. .......... 15/104.94 |
| 5,253,382 A | * | 10/1993 | Beny ........................... 15/22.1 |
| 5,263,218 A | * | 11/1993 | Giuliani et al. .............. 15/22.1 |
| 5,365,627 A | * | 11/1994 | Jousson et al. .............. 15/22.1 |
| 5,369,831 A | * | 12/1994 | Bock ........................... 15/22.1 |
| D361,209 S | * | 8/1995 | Curtis et al. ................. D4/104 |
| 5,617,602 A | * | 4/1997 | Okada ......................... 15/22.1 |
| 5,737,792 A | * | 4/1998 | Quigless .................... 15/167.1 |
| 5,794,295 A | * | 8/1998 | Shen ........................... 15/22.1 |
| 6,079,075 A | * | 6/2000 | Velez-Juan ................. 15/167.1 |

\* cited by examiner

Primary Examiner—Mark Spisich

(57) ABSTRACT

This invention relates to a battery powered electric toothbrush whose toothbrush head can vibrate laterally relative to the longitudinal axis of the toothbrush. The electric toothbrush comprises a handle containing a drive head eccentrically mounted to a motor shaft, a toothbrush head, and a sleeve intermediate the toothbrush head and the handle accommodating a swing arm. The swing arm has a head portion adjoining the toothbrush head pivotally attached in the forward end of the sleeve and has a tail portion provided with a transverse groove receiving the drive head. The head portion of the swing arm is bent to facilitate itself in contact within the forward end of the sleeve to minimize the impact on the motor power as a user presses the toothbrush head in a daily tooth cleaning. The toothbrush head is attachable, sealed, and secured to the drive portion with a flexible collar member.

8 Claims, 4 Drawing Sheets

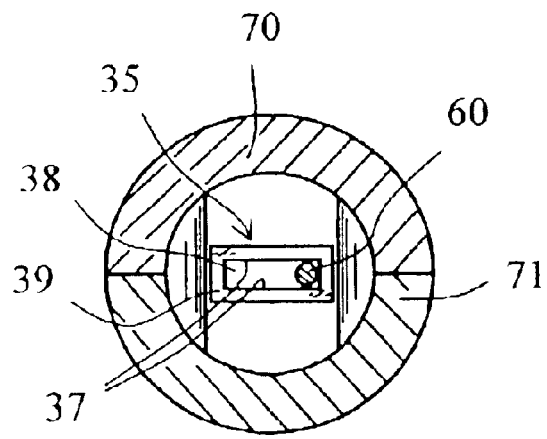
FIG. 6
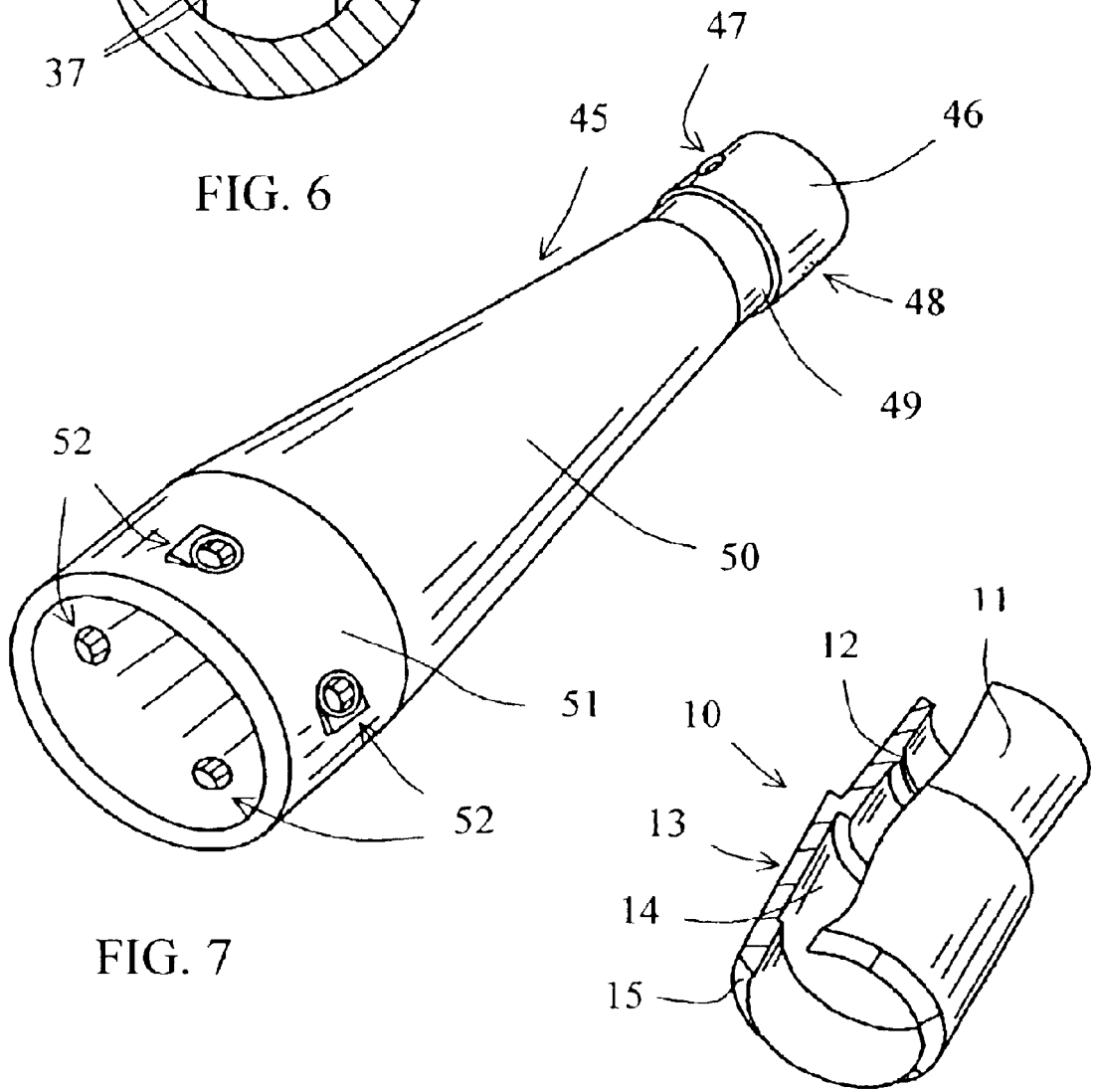
FIG. 7
FIG. 8

VIBRATORY ELECTRIC TOOTHBRUSH

BACKGROUND OF THE INVENTION

The present invention relates to electric toothbrushes, more particularly this invention is an improvement in the structure of a vibratory electric toothbrush whose head can vibrate laterally with respect to the longitudinal axis of the toothbrush.

The benefit of using an electrically operated toothbrush to clean one's teeth is well known and has resulted in many innovations for electric toothbrushes. However, there have been not many innovations that are related to vibratory electric toothbrushes. A vibratory electric toothbrush generally comprises an electric motor, a mechanism that translates the motor movement into lateral vibratory movement, a toothbrush head mounted with plurality of bristles which deliver the vibratory movement onto user's teeth, a battery source, and a holder that holds all parts in a workable condition. When such a vibratory electric toothbrush is operated in a daily tooth cleaning, the toothbrush head and the bristles vibrate laterally with respect to the longitudinal axis of the toothbrush and moves approximately in a plane parallel to the tooth surface. Since the vibratory movement in the bristles can be adapted to the up-and-down movement along tooth gaps by a user holding the toothbrush horizontally in the tooth cleaning, this kind of electric toothbrush has an advantage of effectively cleaning in tooth gaps as well as cleaning the tooth surfaces with minimum hurting to the gums between user's teeth.

U.S. Pat. No. 2,439,262 for a Power-Operated Mechanism discloses a hand manipulable device applicable to a vibratory electric toothbrush having a motion translating mechanism that translates rotary movement into rocking movement. The motion translating mechanism generally comprises a handle, a drive pin within the handle eccentrically extended to a driven shaft which is rotated by an external source during its operation, and a rock arm, pivotally attached in one end of the handle by a spheroidal bearing, having a working end portion projecting beyond the end of the handle to drive an applicable head and having a head at the other end provided with a transverse slot which receives the drive pin. When the mechanism is operated, the drive pin circulates and slides in the slot of the rock arm head and causes rocking movement in the arm. To restrict the rock arm to move in a plane, two spaced-apart guiding walls are provided for the rock arm. The mechanism is substantially simple in structure for translating the rotary movement into the rocking movement, but it is not sufficiently energy efficient since the mechanism employs the guiding walls and the spheroidal bearing that require several substantial contacts between static parts and moving parts which cause an additional energy loss due to the friction while the mechanism is operated. Hence it is not suitable for a portable electric toothbrush powered by a battery that needs better energy efficiency.

U.S. Pat. No. 5,365,627 for a Stem Brush With Automatic Insertion System discloses a joint structure of a handle and a stem brush connection for an oral hygiene device. The structure generally comprises a pair of keys on a motor driven shaft in a handle, a radially extending flange on the base of the shaft, and a receiving portion in a stem brush which comprises a bore to receive the shaft, slots to receive the keys, a pair of ramping sleeves to guide the keys into the slots, and a pair of flexible arms having a recess to receive the flange on the base of the shaft. Although the system has an advantage of easy connection of the handle to the stem brush, it has a drawback of a gap left between the handle and the stem brush, which allows fluids to leak into the handle that degrades its hygienic function since bacteria may grow inside the handle.

BRIEF SUMMARY OF THE INVENTION

One object of the present invention is to provide an improved electric toothbrush powered by battery that can generate lateral vibratory movement in the toothbrush head with respect to the longitudinal axis of the toothbrush. The mechanism generally comprises a toothbrush head and a swing arm pivotally attached in the forward end of a sleeve whose other end is longitudinally attached to a toothbrush handle. The swing arm comprises a tail portion and a head portion and an elongated middle portion intermediate the tail portion and the head portion. The tail portion of the swing arm has a transverse groove with an elongated opening to receive a drive head mounted eccentrically to the motor shaft aligned within the toothbrush handle; and the head portion extending to the toothbrush head has a transverse bore penetrating therein to receive a pivotal pin for the pivotal attachment of the swing arm to the forward end of the sleeve. As an electric toothbrush with this structure is operated, the drive head circulates in a plane approximately perpendicular to the axis of the motor shaft and slides in the transverse groove of the swing arm; and the drive head is able to slide freely in the transverse groove in the lengthwise direction of the transverse groove opening without causing the swing arm to move, but pushes back and forth within the transverse groove in the other direction perpendicular to the first said direction, which causes the swing arm and the toothbrush head to vibrate laterally or to swing with the pivot pin as a fulcrum.

Another object of the invention is to provide an electric toothbrush that is simple in construction and effective in transforming electric energy into useful vibratory movement in the toothbrush head. The structure of the head portion of the swing arm in the present invention is invented for two major working characteristics: first, the head portion of the swing arm is bent from the longitudinal axis thereof to cause the toothbrush head to be inclined from the longitudinal axis of the swing arm, which is desirable in cleaning user's back teeth; secondly, there is a lateral prominent point portion on the lower part of the head portion, distal from the toothbrush head. This prominent point portion is in contact with the inner wall proximal thereto in the forward end of the sleeve when a user presses the bristles in the toothbrush head against teeth as in a daily tooth cleaning. The contact helps to dissipate the force generated by the user's pressing of the bristles against teeth with minimum impact on the motor power.

Still another object of the invention is to provide an electric toothbrush having a toothbrush head that is attachable, secured, and sealed to a drive portion. The toothbrush head in this invention is attachable to the drive portion and is secured by a flexible collar member. The toothbrush head has a base portion mounted with plurality of bristles and a neck portion extended downward to the base portion. A recess with an opening at the free end of the neck portion is provided within the toothbrush head to receive an extension in the head portion of the swing arm. An annular recess is transversely positioned on the neck portion to receive an annular inward projection in the collar member for the secured attachment of the toothbrush head to the drive portion. The collar member also serves as a waterproof means to prevent liquids from leaking into the drive portion by covering the joint gap between the toothbrush head and the end of the drive portion adjoining the toothbrush head.

BRIEF DESCRIPTION OF THE DRAWINGS

FIG. 6 is an enlarged cross sectional view of the same vibratory electric toothbrush taken along the plane VI—VI of FIG. 2;

FIG. 7 is an enlarged perspective view of a sleeve of the same vibratory electric toothbrush shown in FIG. 2;

FIG. 8 is an enlarged perspective view of a collar member with a small portion being broken away of the same vibratory electric toothbrush shown in FIG. 2.

DETAILED DESCRIPTION OF THE INVENTION

Figure 1:
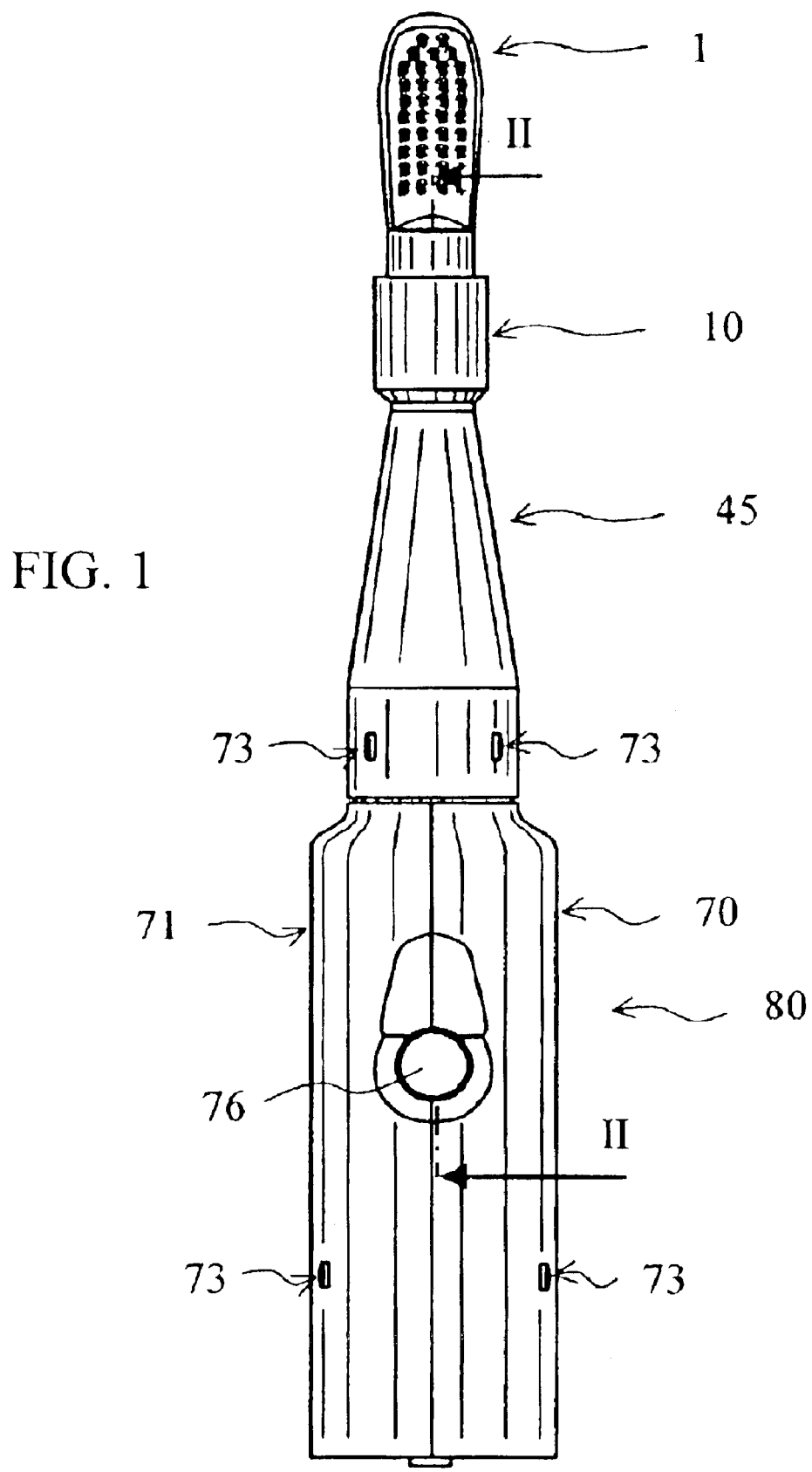
FIG. 1 is a front plan view of a vibratory electric toothbrush according to the present invention.
Figure 2:
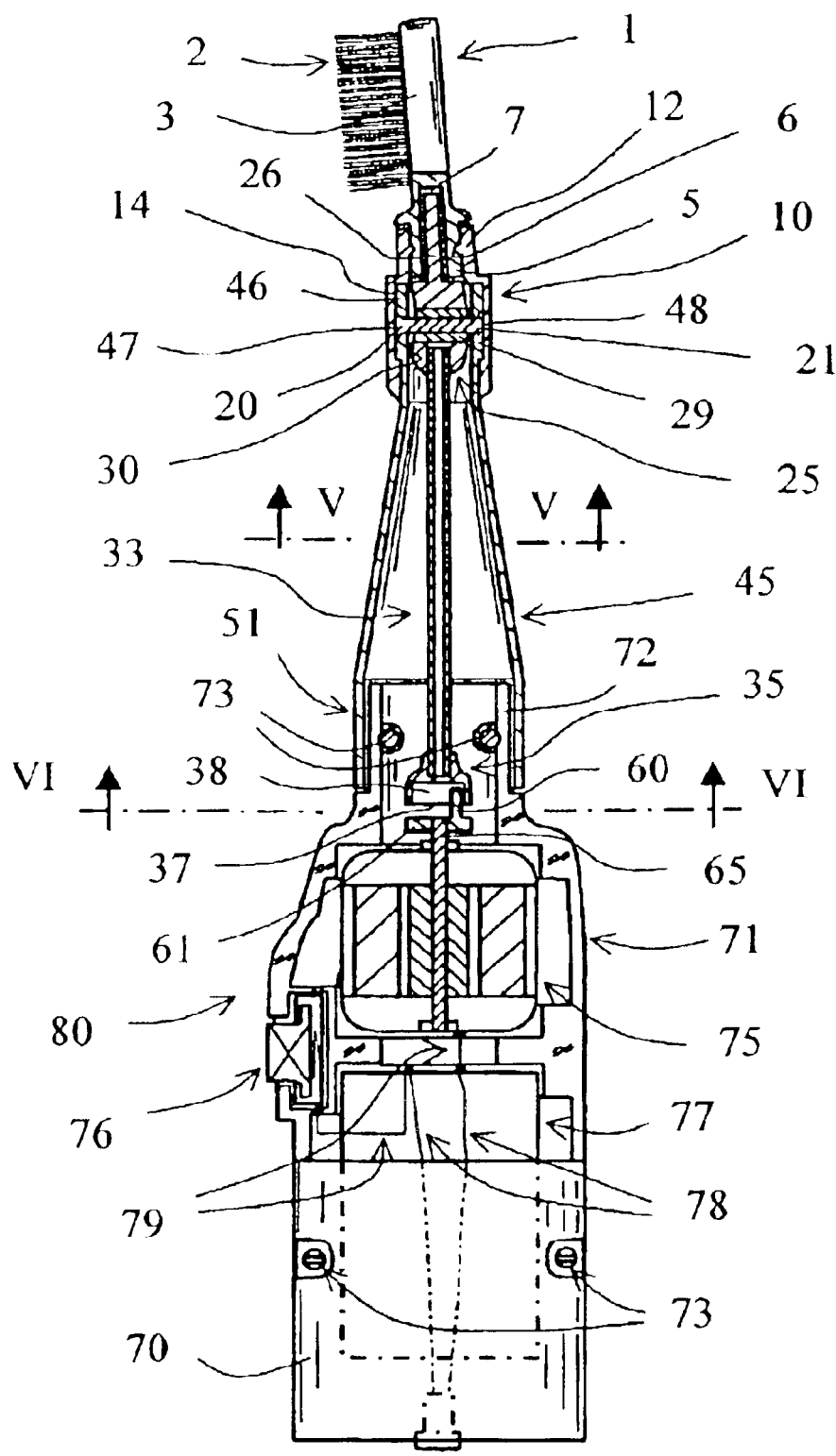
FIG. 2 is a side sectional view of the same vibratory electric toothbrush taken along the plane II—II of FIG. 1.

FIGS. 1 and 2 shows a preferred embodiment of the present invention of a vibratory electric toothbrush which comprises a toothbrush head 1, a swing arm 33, a sleeve 45, a collar member 10, and a handle portion 80 generally included within an elongated case of two covers 70 and 71 preferably made of plastic material and secured by screws 73. Within the handle portion 80 are an electric motor 75 whose motor shaft 65 is in alignment therein, a disk member 61 having a drive head 60 and a bore at its center tightly receiving the motor shaft 65, an electric switch 76, a rechargeable battery pack 77, charging leads 78, and electric wires 79 connected in a workable condition well known in the art.

The sleeve 45 is an elongated hollow body that has a forward end 46 holding the swing arm 33 by a pivotal pin 20 and has a base portion 51 to be attached uprightly to the handle portion 80. The swing arm 33 disposed in the sleeve 45 is an elongated body having a head portion 25 at one end thereof and a tail portion 35 at the other end thereof The swing arm 33 is pivotally attached in the head portion 25 thereof to the forward end 46 of the sleeve 45 by a pivotal pin 20. The pivotal pin 20 is preferably threaded on the front head thereof, as indicated by the reference numeral 21, to secure the attachment thereof An extension 26 in the head portion 25 of the swing arm 33 projects beyond the forward end 46 of the sleeve 45 and is received by a recess 7 in the toothbrush head 1. The tail portion 35 of the swing arm 33 is provided with a transverse groove 38 that receives the drive head 60. The drive head 60 generally in thin cylindrical form is extended vertically and eccentrically to the disk member 61 which is mounted vertically at the center thereof onto the motor shaft 65.

A collar member 10 preferably made of rubber covers over the joint gap between the forward end 46 of the sleeve 45 and the toothbrush head 1 for both sealing the joint gap and securing the toothbrush head 1 to the sleeve 45.

Figures 3, 4, 5:
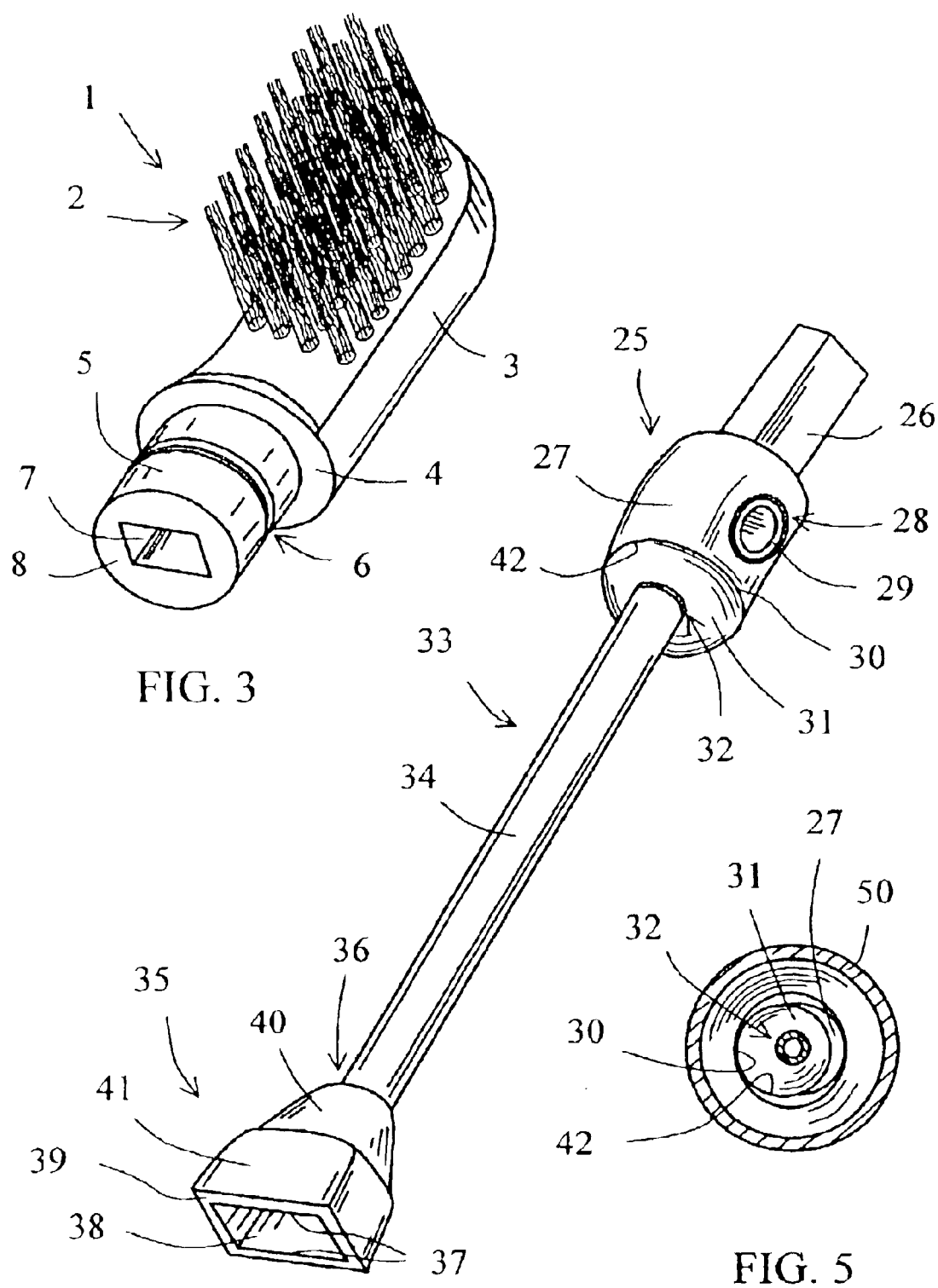
FIG. 3 is an enlarged perspective view of an attachable toothbrush head of the same vibratory electric toothbrush shown in FIG. 2.
FIG. 4 is an enlarged perspective view of a swing arm of the same vibratory electric toothbrush shown in FIG. 2.
FIG. 5 is an enlarged cross sectional view of the same vibratory electric toothbrush taken along the plane V—V of FIG. 2.

The toothbrush head 1, best see in FIG. 3, which is detachable from the vibratory electric toothbrush has a base portion 3 mounted with plurality of bristles similar to the head portion of a manual toothbrush, an annular flange 4 developed longitudinally from the base portion 3 with a diameter matching the width of the base portion 3, and a neck portion 5 extended downward to the annular flange 4 with a cross dimension smaller than the diameter of the flange 4. An annular recess 6 is transversely positioned on the surface of the neck portion 5. The toothbrush head 1 is provided with another recess 7 in alignment therein with an opening at the free end 8 of the neck portion 5.

The swing arm 33, best see in FIG. 4, has a head portion 25, a tail portion 35, and a rod 34 attached to both the head portion 25 at one end thereof and the tail portion 35 at the other end thereof. The rod 34 is an elongated body, which provides a longitudinal axis of the swing arm 33.

The head portion 25 of the swing arm 33 has an extension 26 with a suitable dimension that is snugly contained in the recess 7 in the toothbrush head 1, a spherical portion 31, and a bend cylindrical portion 27 extending at one end thereof to the extension 26 and at the other end thereof to the spherical portion 31. The bend cylindrical portion 27 has a cross dimension approximately equal to that of the neck portion 5 of the toothbrush head 1. The head portion 25 is bent laterally approximately in the middle of the bend cylindrical portion 27. A bore 28 penetrating transversely through the body of the bend cylindrical portion 27 is positioned approximately at the middle of the bending thereof and is in alignment within the same. A bearing means or bushing 29 with suitable length is placed in the bore 28 of the head portion 25 by a pressed fit. The bearing means 29 snugly receives the pivotal pin 20.

The spherical portion 31 has a spherical exterior. A recess 32 in the head portion 25 with an opening on the spherical portion 31 is approximately positioned perpendicularly to and pointing to the middle of the bore 28 and has a depth reaching near but not touching the bore 28 to receive one end of the rod 34 by a pressed fit.

A front point portion 30 is the most distal one from the opening of the recess 32 on the spherical portion 31 along the inner portion of the borderline 42 formed between the bend cylindrical portion 27 and the spherical portion 31, see FIG. 5. The front point portion 30 is laterally prominent over the head portion 25 mainly due to the bending of the head portion 25 and facilitates itself in contact with the inner wall proximal thereto in the forward end 46 of the sleeve 45.

The head portion 25 of the swing arm 33 is preferably made first by molding with plastic material to make the desired portion without the bearing means 29 and then by press fitting the bearing means 29 into the bore 28.

The rod 34 of the swing arm 33 is an elongated body preferably made of stainless steel in tubular form or other materials having the working characteristic of effectively delivering the vibratory energy from the tail portion 35 to the head portion 25 through the rod 34.

The tail portion 35 has a base portion 41 that is transversely elongated and has a tapered portion 40 that is extended upwardly and symmetrically to the base portion 41 with generally a spherical surface on top thereof The tail portion 35 is provided with a transverse groove 38 in alignment within the base portion 41 with an elongated opening at the free end 39 thereof The transverse groove 38 has an elongated cross dimension as the elongated opening thereof at the free end 39 with a length corresponding to the throw of the drive head 60 and a width slightly larger than the diameter of the drive head 60, see FIG. 6. The transverse groove 38 sufficiently receives the drive head 60 and allows the same movable freely therein along the long edges 37 thereon, or in the lengthwise direction of the elongated opening thereof A recess 36 with an opening at the top of the tapered portion 40 is provided in alignment within the same with a depth reaching near but not touching the transverse groove 38 to receive the other end of the rod 34 by a pressed fit. The tail portion 35 is preferably made of plastic material.

The swing arm 33 is preferably assembled by first press fitting one end of the rod 34 into the recess 32 of the head portion 25 and then by press fitting the other end of the rod 34 into the recess 36 of the tail portion 35 with the alignment of the bore 28 being parallel to the long edges 37 on the transverse groove 38 in the tail portion 35.

The extension 26 in the head portion 25 of the swing arm 33 is inclined with respect to the longitudinal axis of the swing arm 33. This inclination of the extension 26 in present embodiment is caused by the bending of the head portion 25 and results in bowing down in the toothbrush head 1 toward the tail portion 35 of the swing arm 33.

The sleeve 45, best see in FIG. 7, is hollow and has a base portion 51, a tapered portion 50 extended upwardly to the base portion 51, an intermediate portion 49 extended upwardly to the end having smaller cross dimension of the tapered portion 50, and a forward end 46 extended upwardly to the intermediate portion 49.

The forward end 46 is enlarged outwardly and has a uniform hollow interior as that of the intermediate portion 49 which is hollow. The interior cross dimension of the forward end 46 of the sleeve 45 is only slightly larger than the overall cross dimension of the head portion 25 of the swing arm 33 to prevent other movement in the head portion 25. A pair of diametric bores 47 and 48 penetrates transversely through the walls of the forward end 46 to receive the pivotal pin 20 on which the swing arm 33 is pivotally attached therein. The bore 48 is preferably threaded to receive the threaded front head 21 of the pivotal pin 20 for secured attachment of the same.

The tapered portion 50 is hollow and has a larger dimension at one end that matches the base portion 51 and gradually becomes smaller toward the other end that matches the intermediate portion 49. The base portion 51 is hollow with a suitable cross dimension that snugly receives the head portions 72 in the handle portion 80 and allows the swing arm 33 to swing freely therein. Two pairs of coaxial bores 52 transversely penetrate the base portion 51 to receive the screws 73 for securing the attachment of the sleeve 45 to the handle portion 80. The sleeve 45 is preferably molded with plastic material and then threaded in the bore 48.

The collar member 10, best see in FIG. 8, comprises two hollow cylindrical portions extended longitudinally to each other, an upper portion 11 covering the neck portion 5 of the toothbrush head 1 and a lower portion 13 covering over the forward end 46 of the sleeve 45. The exterior of the upper portion 11 evenly matches the annular flange 4 of the toothbrush head 1. To the inner surface of the upper portion 11 is extended inwardly and transversely an annular projection 12 that is snugly received by the annular recess 6 on the neck portion 5 of the toothbrush head 1. The lower portion 13 has a beveled end 15 to smooth the edge to the intermediate portion 49 of the sleeve 45. An annular recess 14 is positioned transversely in the inner wall of the lower portion 13 close to the upper portion 11 and receives the forward end 46 of the sleeve 45. The upper portion 11 of the collar member 10 is preferably made to be inclined with respect to the lower portion 13 to match the inclination in the extension 26 of the swing arm 33. The collar member is preferably made of flexible materials such as rubber.

The vibratory electric toothbrush is preferably assembled in the following procedure. First, the middle portion including the sleeve 45 of the vibratory electric toothbrush is assembled by inserting the swing arm 33 into the sleeve 45 with the head portion 25 of the swing arm 33 being close to the forward end 46 of the sleeve 45 and the tail portion 35 being close to the base portion 51, then the bore 28 in the head portion 25 of the swing arm 33 is aligned with the bores 47 and 48 in the forward end 46 of the sleeve 45, and then the pivotal pin 20 is inserted into the bore 47 and pushed through the head portion 25 and finally tightened to the bore 48;

Secondly, the handle portion 80 is assembled by placing in covers 70 and 71 with the electric motor 75 whose motor shaft is tightly attached with the disk member 61, the rechargeable battery pack 77, the electric switch 76, the charging leads 78, and electric wires 79 connected in a workable condition;

Thirdly, the sleeve 45 attached with the swing arm 33 in the forward end 46 is attached to the handle portion 80 by inserting the head portions 72 of the handle portion 80 into the base portion 51 thereof with the transverse groove 38 in the swing arm 33 sufficiently receiving the drive head 60 in the disk member 61. The attachment completes by tightening the covers 70 and 71 with the screws 73;

And finally, the lower portion 13 of the collar member 10 is placed over the forward end 46 of the sleeve 45, then the toothbrush head 1 is attached to the extension 26 of the swing arm 33 by inserting the neck portion 5 of the toothbrush head 1 snugly into the upper portion 11 of the collar member 10. In the assembling, alignments are made to ensure that the extension 26 of the swing arm 33, the upper portion 11 of the collar member 10, and the toothbrush head 1 are all inclined in the same direction and that the face with the bristles 2 of the base portion 3 of the toothbrush head 1 bows down toward the handle portion 80 of the vibratory electric toothbrush.

As the vibratory electric toothbrush is operated, the drive head 60 engaged in the transverse groove 38 of the swing arm 33 circulates in a plane approximately perpendicular to the longitudinal axis of the handle portion 80. The circular motion of the drive head 60 is composed of two motion components perpendicular to each other. The first component parallel to the long edges 37 on the transverse groove 38 does not cause the swing arm 33 to move since the drive head 60 slides freely in the transverse groove 38 in the lengthwise direction of the same, but the second motion component causes the swing arm 33 to move back and forth generally in the direction perpendicular to the first motion component. Hence the toothbrush head 1 attached to the swing arm 33 vibrates or swings laterally with the pivotal pin 20 as a fulcrum while the motor shaft 65 rotates.

When a user presses the bristles 2 in the toothbrush head 1 of the vibratory electric toothbrush against teeth as in a daily tooth cleaning, a force in the pressed direction exerts on the toothbrush head. This force, otherwise is harmful to the operation of the electric toothbrush, is dissipated mainly by the means of the contacting of the front point portion 30 on the head portion 25 of the swing arm 33 with the inner wall proximal to the same in the forward end 46 of the sleeve 45 with minimum impact on the motor power.

Thus the invention has been described with the preferred embodiment being disclosed for illustrative purposes. It should be understood that modifications or variations in the embodiment may be made within the scope of the appended claims.

I claim:

1. A vibratory electric toothbrush comprising:

a toothbrush head having plurality of bristles;

a handle portion having a case accommodating an electric switch, a battery power source, an electric motor, and a drive head mounted eccentrically to the motor shaft;

a sleeve intermediate the toothbrush head and the handle portion having a smaller cross dimension at the forward end thereof adjoining the toothbrush head than that of the other end thereof extending to the handle portion and having a pair of diametric bores in the forward end thereof to support a pivotal means;

a swing arm disposed in said sleeve having a head portion at one end thereof extending to the toothbrush head and pivotally attached in said forward end of said sleeve and having a tail portion at the other end thereof provided with a transverse groove with an elongated opening to receive the drive head which can slide freely in said transverse groove in the lengthwise direction of the elongated opening but is restricted to move relative to said transverse groove in the other direction, perpendicular to the first said direction; and a flexible collar member covering over the joint gap between the toothbrush head and said forward end of said sleeve;

whereby the toothbrush head swings laterally around the pivotal means as the drive head circulates in the transverse groove of said swing arm.

2. The vibratory electric toothbrush of claim 1 wherein the toothbrush head is attachable to said swing arm and has a base portion mounted with plurality of bristles, an annular flange developed from the base portion, a neck portion extended to the flange, an annular recess on the neck portion for the secured attachment thereof, and another recess positioned therein with an opening at the free end of the neck portion to receive an extension in the head portion of said swing arm.

3. The vibratory electric toothbrush of claim 2 wherein said toothbrush head is secured to the vibratory electric toothbrush by said annular recess on said neck portion thereof snugly receiving an annular projection extended inwardly to the inner surface of said collar member.

4. The vibratory electric toothbrush of claim 3 wherein the collar member is secured to said sleeve by an annular recess therein receiving and holding an outward enlargement portion on the forward end of said sleeve.

5. The vibratory electric toothbrush of claim 1 wherein the head portion of said swing arm is bent laterally toward the inner wall of said forward end of said sleeve.

6. The vibratory electric toothbrush of claim 1 wherein the swing arm has a rod intermediate said head portion and said tail portion, one end of the rod is received by a recess in said head portion and the other end of the rod is received by a recess in said tail portion.

7. The vibratory electric toothbrush of claim 1 wherein the sleeve is attachable at a base portion thereof to said handle portion and is provided with at least two bores transversely positioned through the walls of the base portion thereof for secured attachment to the same by screws.

8. The vibratory electric toothbrush of claim 1 wherein the forward end of said sleeve is enlarged outwardly and the pair of diametric bores transversely positioned through the walls thereof to support a pivotal means.

* * * * *